(12) United States Patent
Kirn

(10) Patent No.: US 8,911,505 B2
(45) Date of Patent: Dec. 16, 2014

(54) PROSTHETIC SOCKET STABILIZATION APPARATUS AND TECHNIQUE

(75) Inventor: Larry Joseph Kirn, Austin, TX (US)

(73) Assignee: Articulate Labs, Inc., Austin, TX (US)

( * ) Notice: Subject to any disclaimer, the term of this patent is extended or adjusted under 35 U.S.C. 154(b) by 25 days.

(21) Appl. No.: 12/949,421

(22) Filed: Nov. 18, 2010

(65) Prior Publication Data

US 2011/0118853 A1    May 19, 2011

Related U.S. Application Data

(60) Provisional application No. 61/262,733, filed on Nov. 19, 2009.

(51) Int. Cl.
| | | |
|---|---|---|
| *A61F 2/80* | (2006.01) | |
| *A61F 2/76* | (2006.01) | |
| *A61B 5/103* | (2006.01) | |
| *A61B 5/00* | (2006.01) | |
| *A61F 2/78* | (2006.01) | |
| *A61N 1/04* | (2006.01) | |
| *A61N 1/08* | (2006.01) | |
| *A61N 1/36* | (2006.01) | |
| *A61B 5/11* | (2006.01) | |
| *A61F 2/50* | (2006.01) | |

(52) U.S. Cl.
CPC ............ *A61F 2/80* (2013.01); *A61B 5/1038* (2013.01); *A61B 5/6811* (2013.01); *A61F 2/76* (2013.01); *A61F 2/7812* (2013.01); *A61N 1/0452* (2013.01); *A61N 1/0472* (2013.01); *A61N 1/0492* (2013.01); *A61N 1/08* (2013.01); *A61N 1/36003* (2013.01); *A61N 1/36014* (2013.01); *A61B 5/0048* (2013.01); *A61B 5/1114* (2013.01); *A61B 5/6828* (2013.01); *A61B 5/6829* (2013.01); *A61B 5/6843* (2013.01); *A61B 2562/0219* (2013.01); *A61F 2002/5026* (2013.01); *A61F 2002/5027* (2013.01); *A61F 2002/5036* (2013.01); *A61F 2002/762* (2013.01); *A61F 2002/7635* (2013.01); *A61F 2002/764* (2013.01); *A61F 2002/7655* (2013.01); *A61F 2002/802* (2013.01); *A61N 1/0476* (2013.01)
USPC ............................................. 623/33; 623/24

(58) Field of Classification Search
USPC ............ 623/24, 25, 27, 32, 33, 34, 35, 36, 37
See application file for complete search history.

(56) References Cited

U.S. PATENT DOCUMENTS

| | | | | |
|---|---|---|---|---|
| 5,314,495 | A * | 5/1994 | Kovacs ............................ | 623/25 |
| 5,413,611 | A * | 5/1995 | Haslam et al. ................... | 623/25 |
| 6,500,210 | B1 * | 12/2002 | Sabolich et al. ................. | 623/24 |
| 7,150,762 | B2 * | 12/2006 | Caspers ........................... | 623/33 |
| 2004/0039454 | A1 * | 2/2004 | Herr et al. ........................ | 623/39 |
| 2005/0192676 | A1 * | 9/2005 | Sears et al. ...................... | 623/24 |
| 2006/0155385 | A1 * | 7/2006 | Martin ............................. | 623/24 |
| 2006/0167564 | A1 * | 7/2006 | Flaherty et al. ................. | 623/57 |
| 2008/0200994 | A1 * | 8/2008 | Colgate et al. .................. | 623/24 |
| 2010/0324699 | A1 * | 12/2010 | Herr et al. ........................ | 623/27 |

* cited by examiner

*Primary Examiner* — Marcia Watkins
(74) *Attorney, Agent, or Firm* — Trop, Pruner & Hu, P.C.

(57) ABSTRACT

A portable device, with method, advantageously applies dynamic stimulation of enclosed muscle tissue to stabilize a prosthetic socket on a residual limb. Dynamic stimulation is in response to physical conditions such as prosthesis motion, position and/or internal pressures. Tissue volume contained within the socket may be stabilized by varying average stimulation levels in response to internal socket pressure.

11 Claims, 2 Drawing Sheets

PROSTHETIC SOCKET STABILIZATION APPARATUS AND TECHNIQUE

REFERENCE TO RELATED APPLICATION

This application claims priority to U.S. Provisional Patent Application Ser. No. 61/262,733, filed Nov. 19, 2009, the entire content of which is incorporated herein by reference.

FIELD OF THE INVENTION

This invention relates generally to medical devices, and particularly to apparatus and methods to stabilize a prosthesis through dynamic stimulation of enclosed tissue.

BACKGROUND OF THE INVENTION

Prosthetic devices which replace biological limbs usually interface through a hard cup-shaped shell, referred to as a socket, which encloses a residual limb. In order to transfer the necessary forces, sockets are typically fabricated with composite materials, such as carbon fiber. Compliant materials such as urethane, silicone, and/or cotton or wool fabrics typically are used between the residual limb and socket to cushion and distribute forces within the socket.

Suction is the present preferred method to affix and stabilize the socket to the residual limb. Active regulated vacuum pumps, unidirectional air valves, neoprene sleeves, and silicone suction liners with distal tension pins are among the approaches commonly used to achieve sufficient vacuum to hold sockets to residual limbs. Although usually more effective than earlier mechanical fixation techniques using belts or straps, several factors are not addressed by extant vacuum attachment approaches.

To provide proper force distribution and obtain adequate vacuum for socket stability, minimal clearance inside the socket is required. Residual limbs confined within sockets, however, often undergo changes in volume and sometimes shape as well. Non-contiguous socket shells have demonstrated greater tolerance of volume changes, but attachment remains problematic. To accommodate volume differentials experienced between the residual limb and conventional sockets, one or more fabric layers, or socks, are commonly worn between the limb and socket. Imposition of porous fabric, which does not retain vacuum, has prompted the use of either neoprene sleeves overlaid to seal the juncture between the open socket end and proximal limb, or elastomer skin-contact liners with integral distal tension pins which lock within the socket. Neoprene sleeves used to seal sockets to residual limbs quickly develop pinhole leaks as the edge of the socket is bumped into any non-compliant surface, compromising suction and thus socket stability. Socket liners with distal tension pins stretch longitudinally and thus fail to distribute distal tensile force over the entire residual limb, often creating localized tissue disruption.

Muscles remaining from amputation within a residual limb usually lose the skeletal connection necessary for their original function, so naturally atrophy. In an effort to stabilize residual limb volume, patients are furthermore routinely encouraged to avoid contraction of viable residual muscle. Compliance from the resultant fatty tissue surrounding the bone of a residual limb degrades proprioception, and often impairs prosthetic positional control. This flaccid tissue as well provides little protection for painful distal neuromas, which often form at nerve resection sites. Disuse of residual muscle compounds circulatory issues imposed by amputation, in that muscle activity in biologically intact limbs normally pumps fluids through the body. This results in intolerance to cold temperatures for many amputees, and can exacerbate phantom pain.

Extrinsic muscle stimulation, particularly if applied during contraction, has been repeatedly shown to increase both size and strength of muscle tissue. For this reason, functional muscle stimulation is commonly used to allay atrophy or improve muscle function. This use, however, has been limited to largely pre-programmed stimulation patterns in clinical settings.

A need exists whereby a prosthetic socket may be definitively secured to a residual limb during normal activities, with minimal repercussion on the residual physiology.

SUMMARY OF THE INVENTION

The present invention resides in apparatus and methods for actively stabilizing a prosthesis on a biological limb through dynamic stimulation of residual limb muscle in response to physical conditions of the prosthesis. In addition to biologically enhanced movement and positional control, methods include optional maintenance of residual limb muscle at a relatively constant average volume through stimulation control.

DETAILED DESCRIPTION OF THE INVENTION

Figure 1:
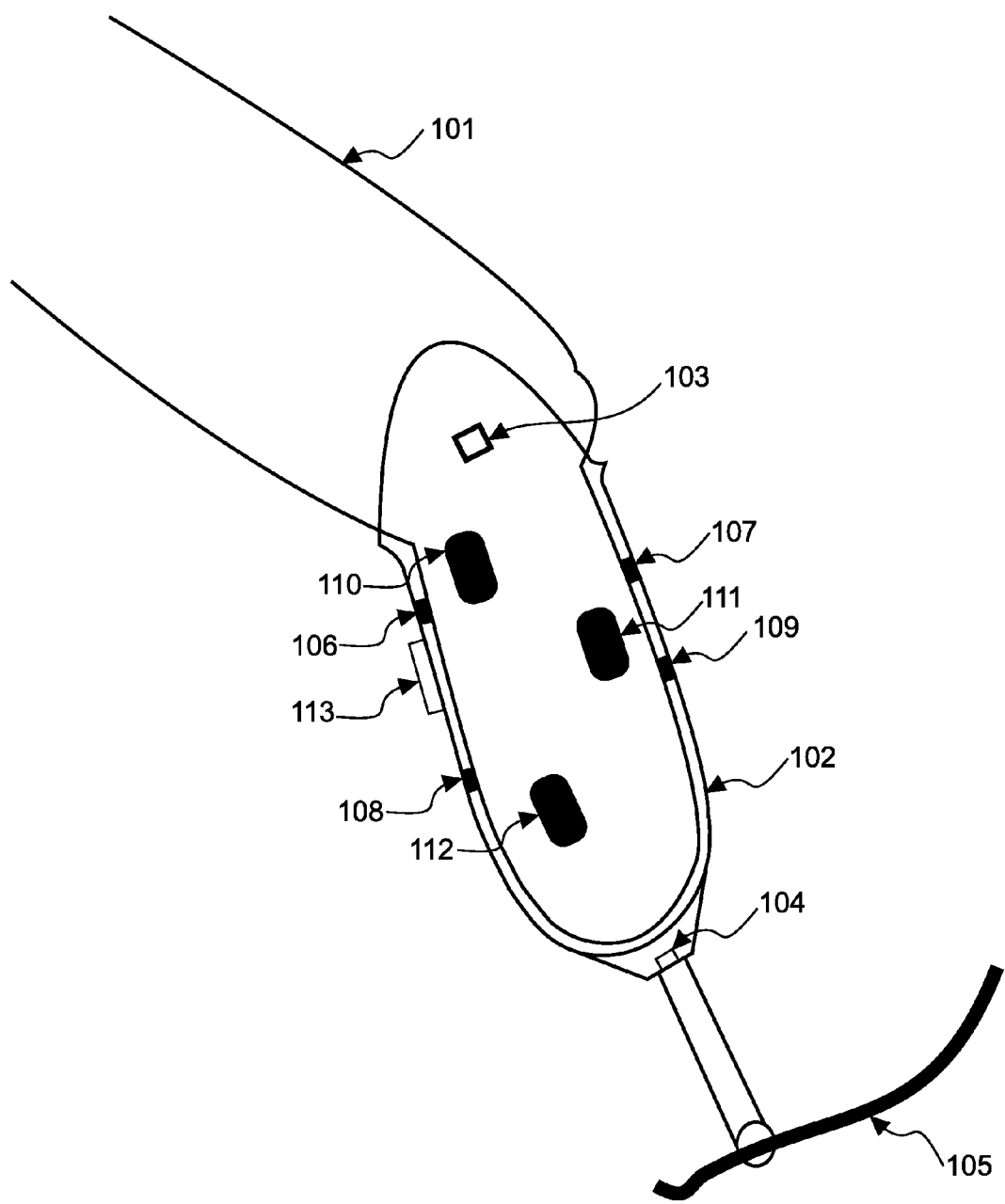
FIG. 1 shows a block diagram of an exemplary embodiment of the present invention.

Referring now to FIG. 1. Prosthetic Socket 102 accepts the residual limb of Human Leg 101. Prosthetic Foot 105 is distally attached to Socket 102, per common practice. Position Sensors 103 and 104 are affixed to Socket 102, and measure spatial orientation and movement. Said Sensors 103 and 104 may be accelerometers, inclinometers, magnetometers, or other means of spatial position or motion sensing, as is known in the art. Force Sensors 106, 107, 108, and 109 are affixed to or are integral with Socket 102, with active sensing surfaces on the interior of said Socket 102. Alternately, one or more of said Pressure Sensors 106, 107, 108, and 109 may be implemented as position sensors sensitive to the relative position of the residual limb of Leg 101 within Socket 102. Controller 113 receives input from said Sensors 103, 104, 106, 107, 108, and 109; and, in response to said sensor inputs, emits high-voltage stimulation pulses to one or more of Stimulation Pads 110, 111, and 112. Pads 110, 111, and 112 are in intimate contact with Leg 101; and may be positioned within or integral to a prosthetic liner, or directly upon the interior surface of Socket 102. Modulation methods for energy to be applied to said Stimulation Pads 110, 111, and 112 may include one or more of amplitude, phase, pulse position, pulse width, frequency, or any other scheme known to the art. Dynamic selection of relative energy to be applied to one or more of said Stimulation Pads 110, 111, and 112 may be determined heuristically by Controller 113 and/or through control design with predefinition of muscle locations to be stimulated within Leg 101. Note that in the absence of a liner, the interior of said Socket 102 may be lined with a compliant material, such as silicone, before pad installation.

Figure 2:
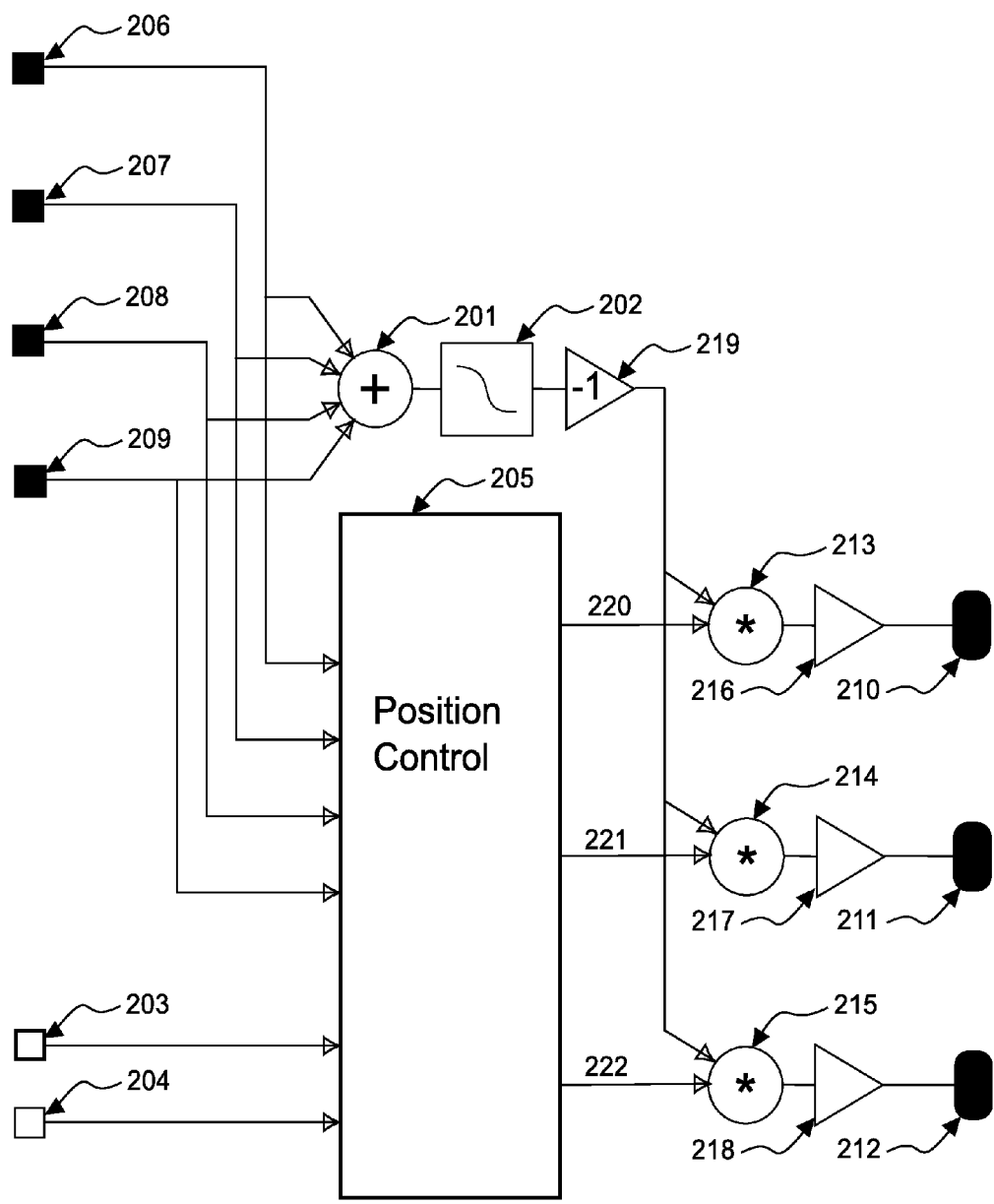
FIG. 2 shows a block diagram of a computational architecture demonstrating use of the present invention within the exemplary embodiment of FIG. 1.

Referring now to FIG. 2, Pressure Sensors 206, 207, 208, and 209 correspond to Pressure Sensors of Sensors 106, 107, 108, and 109 of FIG. 1, respectively. Position Sensors 203 and 204 correspond to Sensors 103 and 104; and Stimulation Pads 210, 211, and 212 correspond to Pads 110, 111, and 112, all of FIG. 1.

Pressure Sensors 206, 207, 208, and 209 provide internal socket pressure indications to Summer 201, and internal socket pressure and/or relative limb position, as noted above, to Positional Control 205. Position Sensors 203 and 204 provide input to Position Control 205 only. Summer 201 provides a signal to Integrator 202 which is representative of the composite force applied to the interior of Socket 102 of FIG. 1. The output of Integrator 202 is inverted by Amplifier 219. Amplifier 219 thus provides an output signal which is inversely proportional to the average composite force within Socket 102, presumably over a period of days or weeks. The output of Amplifier 219 is supplied as common input to Multipliers 213, 214, and 215.

Position Control 205 comprises a positional control scheme, preferably embodied as analog circuitry and/or software executed by a control device, such as a microcontroller or digital signal processor. Under stimulation of said Sensors 206, 207, 208, 209, 203, and/or 204, said Controller 205, through any of control schemes known to the art, provides variable Stimulation Signals 220, 221, and 222 as input to Multipliers 213, 214, and 215, respectively. The outputs of Multipliers 213, 214, and 215 are supplied as input to High-Voltage Drivers 216, 217, and 218, respectively, which in turn provide high-voltage pulses to Stimulation Pads 210, 211, and 212, respectively. In that the common inputs of Multipliers 213, 214, and 215 are provided by Amplifier 219, Stimulation Signals 220, 221, and 222 provided by Position Control 205 are modulated indirectly by the average composite force indicated by Sensors 206, 207, 208, and 209.

Stimulation energy supplied to Pads 210, 211, and 212 is therefore inversely proportional to the average force within Socket 102 of FIG. 1. Stimulation Pads 210, 211, and 212, being in intimate contact with Leg 101 of FIG. 1, induce variable contractions of various leg muscles within Socket 102 of FIG. 1. Being localized, these contractions therefore create vectored forces directly upon Socket 102. It is noted that switching amplification, preferably controlled current or power, may advantageously be used in Drivers 216, 217, and 218.

Under control of said Sensors 206, 207, 208, 209, 203, and/or 204, Position Control 205 calculates appropriate stimulation outputs for application to Pads 210, 211, and 212 which serve to stabilize Socket 102 upon Leg 101 as it is used in normal activities. In that the relative positions of all devices of Socket 102 are fixed, standard control techniques, such as proportional-integral-derivative loops, may determine differential outputs for said Pads 210, 211, and 212. Alternatively, software models of the biological components within Socket 102 may be interposed in the architecture of Position Control 205 between sensor inputs and stimulation output control loops, so as to improve predictive behavior. It is assumed that a state-machine software architecture may be applied to algorithms executed in Position Control 205, selectively using historical data to determine present and future states.

Although depicted separately for the purpose of explanation, integration of the composite functions of Summer 201, Integrator 202, Amplifier 219, and Multipliers 213, 214, and 215 is anticipated with the functions described of Position Control 205, in any of the various possible implementations described above. Use of the current invention can as well be seen to be independent of the type of socket used, specific function of a prosthesis, socket liner use or type, and type of muscle stimulation employed.

It is assumed that Socket 102 of FIG. 1 employs at least one region of negative draft angle, wherein constriction increases with proximal direction. This is necessary to provide leverage upon Socket 102 by the muscles of Leg 101.

By the above discussion, it can be seen that control algorithms or circuitry, using positional and/or force data, may dynamically stabilize a prosthetic socket upon an appendage through stimulation of the contained muscle. In that muscle growth is known to result from stimulated contraction, and average pressure within the socket is roughly proportional to contained volume; it can as well be seen that muscle volume may be stabilized within a prosthetic socket through inclusion of average internal pressure in the control algorithm. Finally, muscle stimulation of the present invention can be seen to inherently follow movement, more closely replicating intact biological activity. Such activity has been shown to reduce phantom sensations, arguably through integrated sensory stimulation, and improve fluid circulation.

The invention claimed is:

1. A system to stabilize a prosthesis affixed to an appendage comprising:
    a shell to contain the appendage and form an interface to the prosthesis;
    means to measure at least one of (a) a spatial attribute of the shell and (b) a force on the shell;
    means to measure average pressure within the shell;
    means to (c) dynamically stimulate at least one area of muscle tissue contained within said shell and (d) stabilize the interface in response to the dynamic stimulation; and
    means to control the dynamic stimulation in response to the average pressure and the at least one of the spatial attribute and the force.

2. The apparatus of claim 1, wherein said means to control the dynamic stimulation comprises at least one of digital circuitry and software executed by a processor.

3. The apparatus of claim 1, wherein said means to measure comprises an accelerometer.

4. The apparatus of claim 1, wherein said means to dynamically stimulate applies electrical stimulation.

5. The apparatus of claim 1, comprising an elastomeric liner to be worn within said shell.

6. The apparatus of claim 1, wherein said means to dynamically stimulate includes switching amplification.

7. A prosthesis comprising:
    first and second sensor nodes; and
    a controller, when coupled to the first and second sensor nodes, configured to perform operations comprising:
        determining a first force, based on the first sensor node, over a first period of time;
        determining an environmental condition based on the second sensor node, wherein the environmental condition (a) corresponds to a shell coupled to an appendage, and (b) comprises force;
        determining a first component of first stimulus energy based on the environmental condition and the first force; and
        stimulating muscle tissue coupled to the prosthetic with the first stimulus energy to stabilize an interface between the appendage and the prosthesis;
        wherein the first component includes pulse amplitude that is inversely proportional to the first force, the first force includes a composite force based on inputs from the first sensor node and at least one of the second sensor node and a third sensor node, and the first force includes an average force based on the inputs.

8. The prosthesis of claim 7, wherein the first period of time extends at least 1 day in duration and the first force includes an average of forces sensed during the first period of time.

9. The prosthesis of claim 7 including a plurality of stimulation nodes and each of the plurality of stimulation nodes receives composite force as an input.

10. A system comprising:
a shell to form an interface between an appendage and a prosthesis;
a plurality of sensors;
a plurality of stimulation nodes; and
a controller configured to couple to the sensors and the shell and (a) determine a spatial attribute and a force, both of which correspond to the shell; (b) determine average pressure corresponding to the shell based on determining the force, (c) stimulate the appendage, via the plurality of stimulation nodes, to stabilize the interface in response to the stimulation; and (d) determine the stimulation in response to the determined spatial attribute, force, and average pressure.

11. The system of claim 10, wherein stimulating the appendage includes electrical stimulation.

\* \* \* \* \*